United States Patent [19]

Morgan et al.

[11] Patent Number: 5,275,157
[45] Date of Patent: Jan. 4, 1994

[54] PULSE FORMING CIRCUITS

[75] Inventors: Carlton B. Morgan, Bainbridge Island; Daniel Yerkovich; Donald C. Maier, both of Seattle, all of Wash.

[73] Assignee: Physio-Control Corporation, Redmond, Wash.

[21] Appl. No.: 685,132

[22] Filed: Apr. 12, 1991

[51] Int. Cl.$^5$ ............................................... A61N 1/00
[52] U.S. Cl. ............................................... 607/6
[58] Field of Search ............... 128/419; 307/540, 545, 307/547, 549, 631; 338/22; 307/310, 264

[56] References Cited

U.S. PATENT DOCUMENTS

| | | | |
|---|---|---|---|
| 3,078,850 | 2/1963 | Schein et al. | 128/419 D |
| 3,219,942 | 11/1965 | Bell | 307/310 X |
| 3,241,555 | 3/1966 | Caywood et al. | 128/419 D |
| 3,359,984 | 12/1967 | Daniher et al. | 128/419 D |
| 3,706,313 | 12/1972 | Milani et al. | 128/419 D |
| 3,866,615 | 2/1975 | Hewson | 128/419 D |
| 3,886,950 | 6/1975 | Ukkestad et al. | 128/419 D |
| 4,155,017 | 5/1979 | Gaule et al. | 307/268 |
| 4,387,291 | 6/1983 | Keppel | 338/22 R X |
| 4,463,268 | 7/1984 | Levinson | 307/106 |
| 4,504,773 | 3/1985 | Suzuki et al. | 128/419 D |
| 4,566,457 | 1/1986 | Stemple | 128/419 D |
| 4,574,810 | 3/1986 | Lerman | 128/419 D |

FOREIGN PATENT DOCUMENTS 1586973  3/1981  United Kingdom ........... 128/419 D

OTHER PUBLICATIONS

R. Ford et al., *Positive temperature coefficient resistors as high-power pulse switches: performance limitations, temperature effects, and triggering behavior*, Journal of Applied Physics 61(6), Mar. 15 1987, pp. 2381–2386.

R. Ford et al., *Application of Non-linear Resistors to Inductive Switching*, IEEE Transactions on Electrical Insulation, vol. E1-20 No. 1, Feb. 1985, pp. 29–37.

*Primary Examiner*—Lee S. Cohen
*Assistant Examiner*—Samuel G. Gilbert
*Attorney, Agent, or Firm*—Christensen, O'Connor, Johnson & Kindness

[57] ABSTRACT

Circuits for controlling the current flow of an energy pulse as a function of the temperature of a resistive element in the circuit so that the current flow varies over time in accordance with a predetermined waveform. The circuits include at least one negative temperature coefficient thermistor connected between an energy storage device and connectors for delivering energy stored in the storage source to an external load. In one embodiment of the invention the circuit includes a second thermistor for shunting a residual portion of the current delivered by an energy pulse away from the external load. In another embodiment of the circuit, a small inductive device is used for adjusting the shape of the predetermined waveform. In yet another embodiment of the device, a plurality of thermistors arranged in a bridge-like configuration are used to control the current of the energy pulse so that its waveform is biphasic. Heat sinks may be attached to the thermistors for cooling the latter so as to increase the rate at which energy pulses may be delivered by the circuits.

23 Claims, 6 Drawing Sheets

PULSE FORMING CIRCUITS

FIELD OF THE INVENTION

This invention relates generally to circuits for forming electrical pulses. More specifically, it relates to circuits for forming such pulses with a determined amplitude, duration, and shape.

BACKGROUND OF THE INVENTION

Electrical pulses have traditionally been shaped using resistors, capacitors, and inductors, so-called RLC circuits, to form pulses having desired rise and fall patterns, amplitudes, and duration. One disadvantage of such prior art circuits, particularly when pulses of relatively large voltages or currents are required, has been the size and weight of the components required. As a consequence of the size and weight of such prior art RLC circuits, the latter are not adapted for use in relatively small pieces of equipment or where the total weight of the piece of equipment must be minimized. For instance, to the extent the weight and size of the pulse-forming circuits in a defibrillator can be reduced, its portability and hence utility will be increased.

Therefore, a strong need exists for novel wave-shaping circuits utilizing solid state devices of relatively small size and weight which are reliable and can produce pulses having desired current wave form on a repeated basis.

SUMMARY OF THE INVENTION

Briefly, in its various embodiments, the invention utilizes a temperature sensitive resistor, such as a thermistor, connected between or across a switched source and a load to shape the electrical pulse supplied to the load. The temperature/resistance characteristics of the resistor are selected so that the shape of the pulse varies in a predetermined manner as a function of the temperature of the resistor. In one particular implementation of the invention, the load can be the transthoracic impedance of a person requiring defibrillation.

BRIEF DESCRIPTION OF THE DRAWINGS

The invention itself is set forth in the claims appended hereto and forming a part of this specification. However, an understanding of the structure and operation of various embodiments of the invention may be had by reference to the detailed description taken in conjunction with the drawings in which:

DETAILED DESCRIPTION OF THE PREFERRED EMBODIMENT

Figure 1:
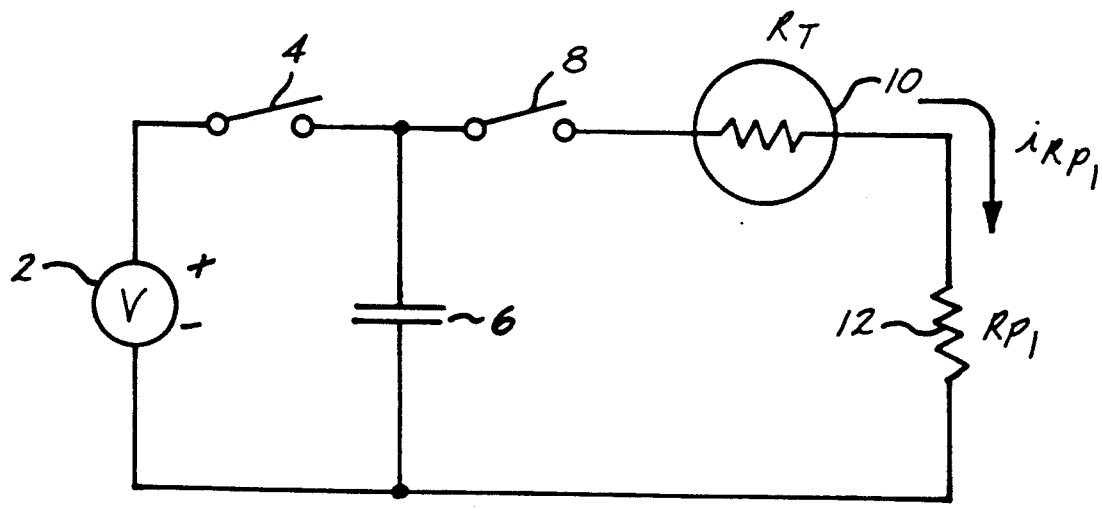
FIG. 1 is a schematic drawing of one embodiment of the invention.

FIG. 1 illustrates a first embodiment of the circuit of the present invention in schematic form. This circuit includes a DC source 2 having its positive terminal connected through a first normally opened switch 4 to one side of a capacitor 6, the other side of which is connected to the negative terminal of the source 2. Connected in parallel with the capacitor 6 is a second normally opened switch 8, a thermistor 10, and a load represented by a resistive element 12. Thermistor 10 is a self-heating thermally active resistive device. Thermistor 10 is selected to have a negative temperature coefficient so that its resistance will decrease as its temperature rises. The load represented by element 12 typically does not form part of the circuit of the present invention, and is shown in the FIGURES merely to illustrate the manner in which the present circuit is coupled with a resistive load.

In an exemplary embodiment of the invention, three series-connected thermistors of the type manufactured by Keystone Carbon Company of St. Mary's, Pa. 15857 and identified by model No. CL-70 may be satisfactorily used as thermistor 10. Also in this embodiment, capacitor 6 is a 37.5 mF capacitor and about a 4,200 volt charge is stored in the capacitor. In connection with the selection of these circuit elements, patient impedance is assumed to be about 50 ohms.

Figure 2:
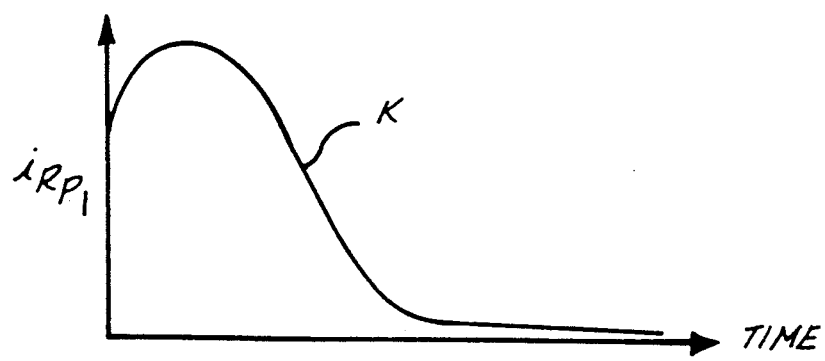
FIG. 2 is a drawing illustrating typical variation in the current against time of the pulse produced by the circuit shown in FIG. 1.

Referring to FIGS. 1 and 2, the circuit illustrated in FIG. 1 may be operated as follows: the switch 4 is closed causing the capacitor 6 to be charged to a value determined by the voltage of the source and the duration of the switch closure. The switch 4 is then opened and switch 8 closed. When the switch 8 is closed the charge on the capacitor 6 is applied to the series circuit of thermistor 10 and load 12. Initially, the resistance of the thermistor 10 is relatively high so that the current to the load 12 is relatively low. However, the initial current flow causes the temperature of the thermistor to rapidly increase, thereby lowering its resistance and causing the current flow through the thermistor to increase. The temperature of the thermistor continues to rise with increases over time in current flow. The rate of change of resistance of the thermistor, and hence the change in magnitude of the current delivered by the pulse, illustrated by waveform K in FIG. 2, is determined by the temperature/resistance characteristics of the selected thermistor and by the heat capacity of the thermistor selected. The temperature of the thermistor will continue to rise until a maximum value of current flow is reached, which value is determined by the amount of the charge on the capacitor 6. As the capacitor continues to discharge through the thermistor and load 12, the current through these elements is reduced.

This effect of thermistor 10 on current flow delivered by the pulse is illustrated graphically in FIG. 2, where the current through the load is plotted against time. Immediately upon the closure of switch 8, the current through the load 12 jumps to a finite value that depends on the initial resistance of thermistor 10 and load 12. As the switch 8 remains closed the current continues to increase until a maximum value is reached. This increase is due to the decreasing resistance of thermistor 10. At the same time the charge on the capacitor 6 is decreasing and at a certain point the current through the load reaches a maximum value and then decreases. The resultant current waveform identified at K in FIG. 2, may be described approximately as a damped sinusoidal wave.

Figure 3:
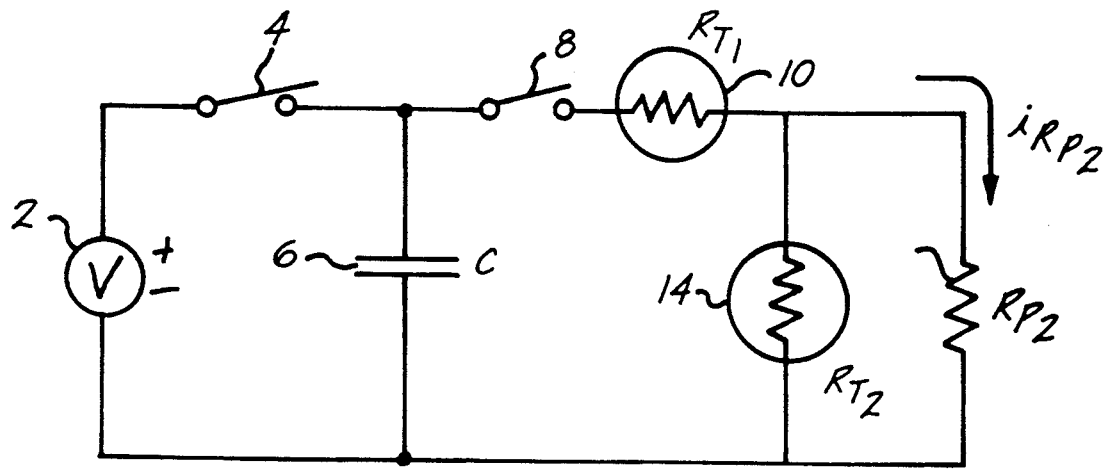
FIG. 3 is a schematic illustration of a second embodiment of the invention.

It is believed to be desirable in the case of defibrillators, and possibly in other applications, to reduce the load current (the patient current in the case of defibrillators) to zero very shortly after the peak value of the current is achieved. To achieve such rapid decrease in the load current, the embodiment of the present invention illustrated in FIG. 3 was developed. The circuit illustrated in FIG. 3 is identical to the circuit illustrated in FIG. 1 and described above, except that a second thermistor 14 is connected in parallel with the load. The thermistor 14 has a negative coefficient of resistance so that the current through it will increase as the temperature of the thermistor increases. In an exemplary embodiment of the circuit illustrated in FIG. 3, three series connected thermistors of the type manufactured by Keystone Carbon Company of St. Mary's, Pa. and identified by model No. CL-70 may be satisfactorily used as thermistor 14.

Figure 4:
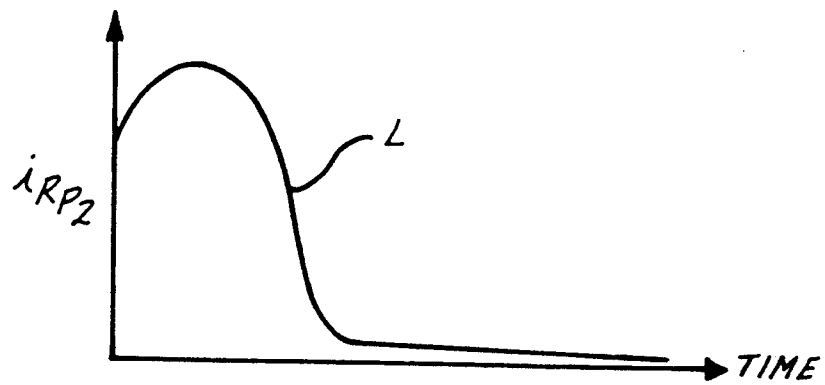
FIG. 4 is a drawing illustrating typical variation in the current against time of the pulse produced by the circuit shown in FIG. 3.

The effect of the circuit illustrated in FIG. 3 on current flow delivered by the pulse is illustrated in FIG. 4, where once again current through the load is plotted against time. The interaction of thermistor 10 and the load occurs in substantially the same manner as with the circuit illustrated in FIG. 1. Initially, the value of thermistor 14 is much larger than the load resistance, so that most of the current flows through the load during initial portions of the pulse, as illustrated in current waveform L. However, as the pulse continues, thermistor 14 heats, its resistance decreases, and the thermistor begins to shunt current away from the load. By the end of the pulse, the resistance of thermistor 14 is much less than the resistance of the load, and as a result the thermistor shunts away from the load almost all of the remaining energy in the capacitor.

Figure 3A:
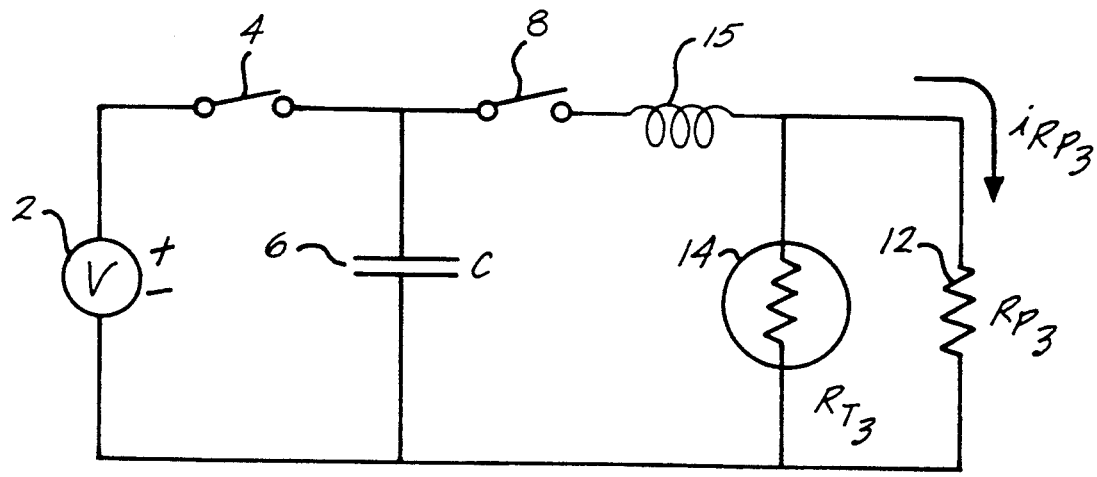
FIG. 3a is a schematic illustration of a third embodiment of the invention.

In some cases, it may be desirable to employ thermistor 14 in a conventional RLC circuit to cause the magnitude of the current delivered by the circuit to decrease more rapidly with respect to time than would otherwise occur. That is, thermistor 14 may be employed in a conventional RLC circuit to perform the shunting function described above in connection with the circuit illustrated in FIG. 3. FIG. 3a illustrates a conventional RLC circuit in which thermistor 14 is connected in parallel with the load so as to shunt residual portions of the energy discharged by capacitor 6 away from the load, as described above with respect to the circuit illustrated in FIG. 3. The circuit illustrated in FIG. 3a differs from the circuit illustrated in FIG. 3 only in that inductor 15 is used in place of thermistor 10. The current flow of the pulse delivered by the circuit illustrated in FIG. 3a will rise and fall substantially in accordance with waveform L illustrated in FIG. 4, except that the current will rise from a lower initial magnitude.

Figure 5:
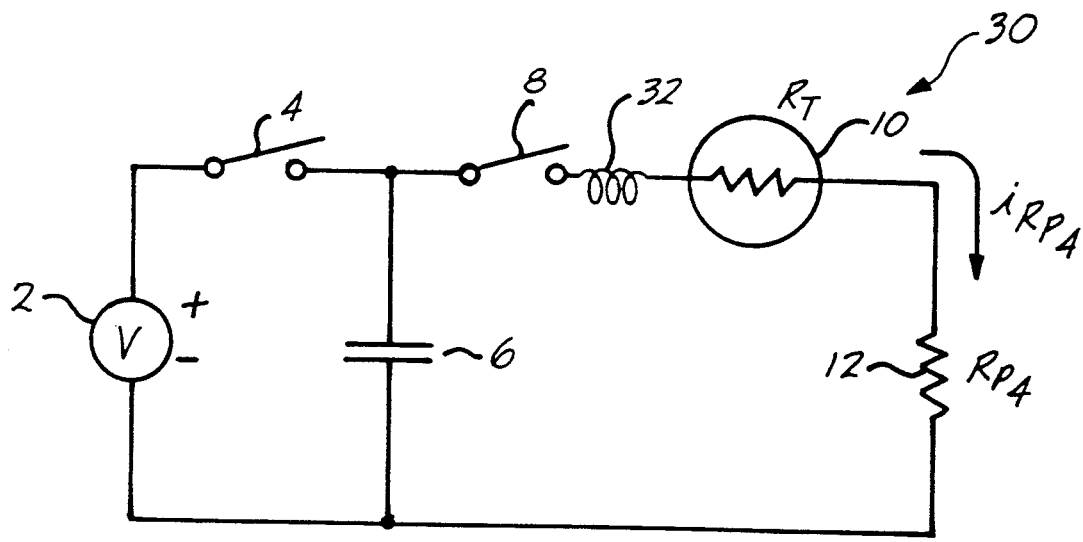
FIG. 5 is a schematic illustration of a fourth embodiment of the invention.
Figure 6:
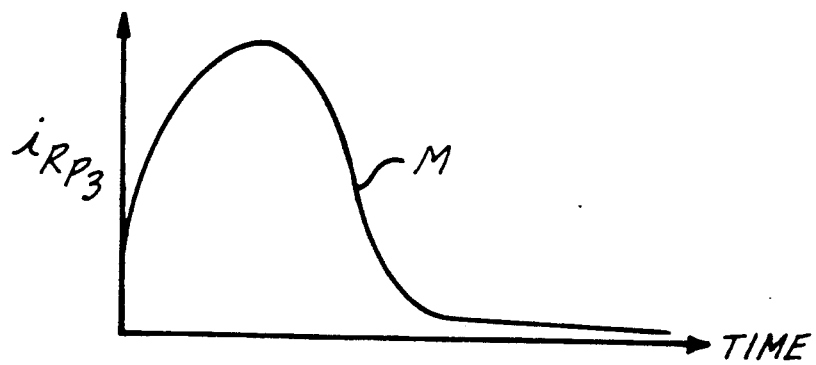
FIG. 6 is a drawing illustrating typical variation in the current against time of the pulse provided by the circuit shown in FIG. 5.

Referring to FIGS. 5 and 6, under certain circumstances it is desired to mimic the damped sinusoidal waveform created by conventional RLC pulse generation circuits of the type employed in known defibrillators more closely than is possible with the circuits illustrated in FIGS. 1 and 3. To this end, the circuit 30 illustrated in FIG. 5 was developed. Circuit 30 is identical to the circuit illustrated in FIG. 1, except that it includes an inductive element 32 connected in series between switch 8 and thermistor 10. In an exemplary embodiment of the present invention, inductive element 32 is a 10 mH inductor.

As illustrated by current waveform M in FIG. 6 the amplitude of the current delivered by the pulse generated by circuit 30 increases more slowly than does the amplitude of the current delivered by the pulses generated by the circuits illustrated in FIGS. 1 and 3. Under certain conditions, this slower increase in the amplitude of the current delivered by a pulse is desired. For instance, when circuit 30 is incorporated in a defibrillator and the pulse the circuit generates is to be delivered to a patient for the purpose of defibrillating the patient's heart, for certain medical conditions it may be desirable that the current delivered by the pulse not increase too rapidly toward a peak value.

Alternatively, inductive element 32 may be employed in the circuit illustrated in FIG. 3. In this case, the inductive element 32 is also connected in series between switch 8 and thermistor 10.

Circuit 30 illustrated in FIG. 5 is slightly heavier and more expensive than the circuits illustrated in FIGS. 1 and 3 due to the inclusion of inductive element 32. However, the circuit does not weigh as much or cost as much as conventional RLC pulse forming circuits which typically include at least one inductive element rated at between 20 mH and 50 mH. In certain circumstances, an ideal balance between weight and cost savings versus circuit performance may be achieved by using circuit 30 illustrated in FIG. 5 in place of the circuits illustrated in FIGS. 1 and 3 or in place of conventional RLC circuits.

Figure 7:
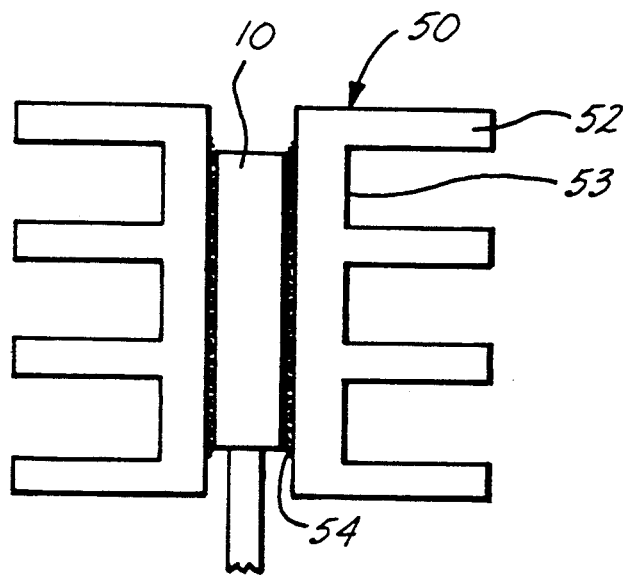
FIG. 7 is a side elevation view of a heat sink attached to front and back surfaces of a thermistor of the type used in the various embodiments of the present invention.
Figure 8:
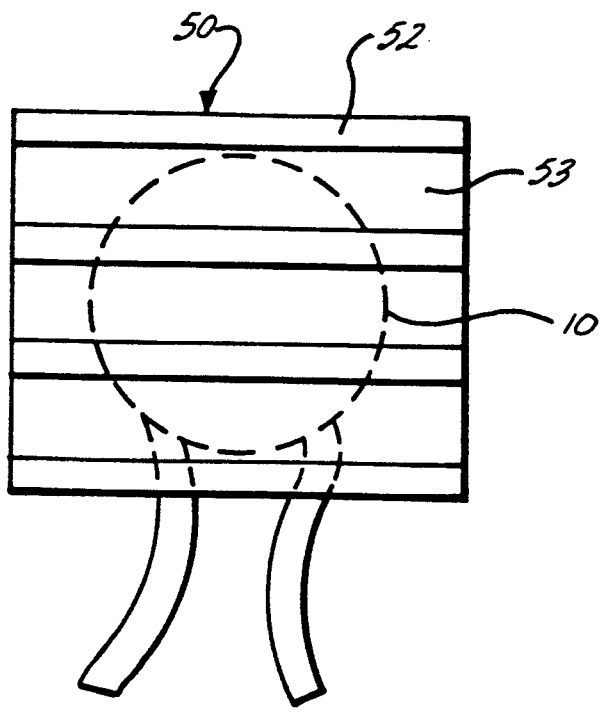
FIG. 8 is a front elevation view of the heat sink and thermistor illustrated in FIG. 7.

Referring to FIGS. 7 and 8, it is frequently desired to apply defibrillation or other pulses repeatedly in short succession to a patient or a load. Under certain conditions, thermistors 10 and 14 in the circuits illustrated in FIGS. 1, 3, and 5 and described above will retain sufficient residual heat between pulses as to prevent the circuits from generating pulses having the current waveform illustrated in FIGS. 2, 4, and 6 and described above. The extent to which the thermistors retain residual heat will vary as a function of the frequency of the pulses, the temperature/resistance characteristics of the thermistors, and the environment in which the thermistors are located.

To minimize this retention of heat, and thereby increase the frequency at which pulses may be applied, heat sinks 50 may be attached to thermistors 10 and 14. Each heat sink 50 includes a plurality of planar fin members 52 which are attached via integral base plate 53 to the front and back surfaces of the thermistor. Such attachment is achieved using a heat conductive bonding agent 54, such as a suitable epoxy. Heat sinks 50 are made from a material having a high thermal conductivity, such as aluminum. By adding heat sinks 50 to thermistors 10 and 14, the latter will cool rapidly, typically in less than about five seconds, thereby allowing rapid application of pulses.

Figure 9:
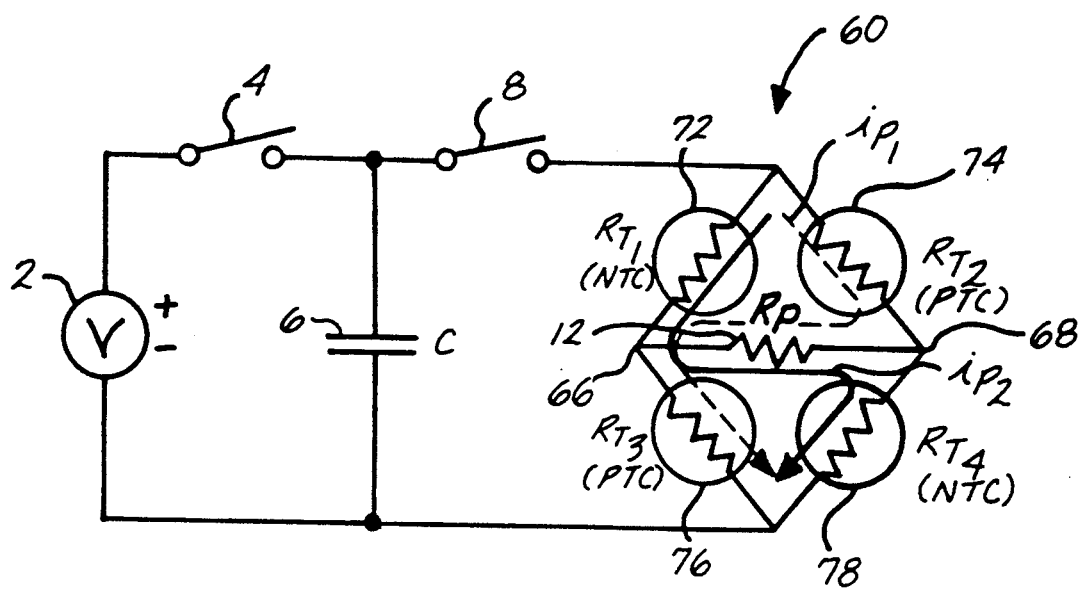
FIG. 9 is a schematic illustration of a fifth embodiment of the invention.
Figure 10:
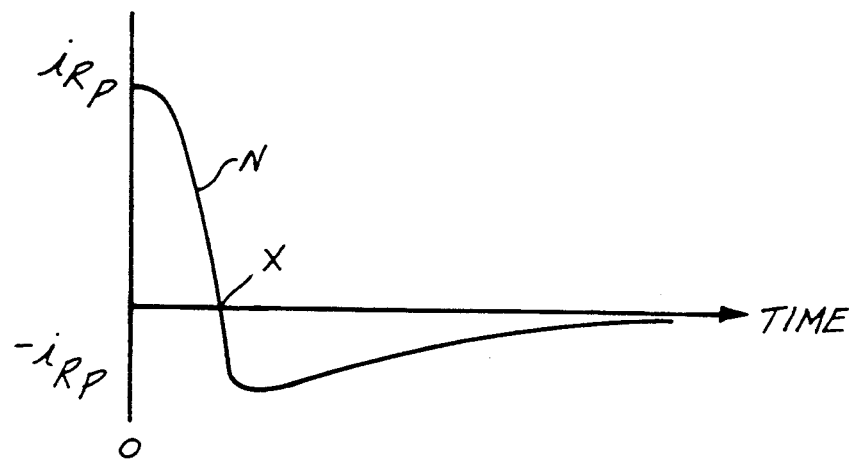
FIG. 10 is a drawing illustrating typical variation in the current against time of the pulse provided by the circuit shown in FIG. 10.

Referring to FIGS. 9 and 10, recently experimental and clinical tests have been performed using defibrillators designed to produce a defibrillation pulse having a biphasic or alternating polarity waveform. This waveform is characterized by the first portion of the pulse having a positive polarity and the second portion of the pulse having a negative polarity, much like the waveform N illustrated in FIG. 10. A circuit for generating a defibrulation pulse having a biphasic waveform, which also possesses the size and weight saving features discussed above in connection with the circuits illustrated in FIGS. 1, 3, 3a, and 5, is illustrated in FIG. 9 and identified at 60.

Circuit 60 is similar to the circuit illustrated in FIG. 1 in that it comprises voltage source 2, switches 4 and 8, and capacitor 6. Additionally, the resistive load with which circuit 60 is designed to be connected is represented by resistive element 12. One side of resistive element 12 is identified by reference numeral 66 and the other side of the resistive element is identified by reference numeral 68. Circuit 60 differs from the circuit illustrated in FIG. 1 in that it includes thermistors 72, 74, 76 and 78 in place of thermistor 10. Thermistors 72 and 78 are negative temperature coefficient thermistors and thermistors 74 and 76 are positive temperature coefficient thermistors. Thermistors 72-78 are coupled with resistive element 12 in a bridge-like configuration, with thermistor 72 being connected between switch 8 and side 66 of resistive element 12, thermistor 74 being connected between switch 8 and side 68 of resistive element 12, thermistor 76 being connected between side 66 of resistive element 12 and the negative polarity side of voltage source 2, and thermistor 78 being connected between side 68 of resistive element 12 and the negative polarity side of voltage source 2. Thermistors 72-78 are selected so that the resistance of thermistor 74 is less than the resistance of thermistor 72 when the thermistors are at ambient temperature, e.g., 25° C., and so that the resistance of thermistor 76 is less than the resistance of thermistor 78 when these thermistors are at ambient temperature. In addition, the thermistors are selected so that thermistors 74 and 76 have nearly identical resistance across substantially the entire temperature spectrum at which they will operate, and so that thermistors 72 and 78 have nearly identical resistance across substantially the entire temperature spectrum at which they will operate.

As a consequence of the bridge-like configuration and the above-discussed thermal/resistive characteristics of thermistors 72-78, when the latter are at ambient temperature, and when switch 8 is closed, current will flow from capacitor 6 along current path $i_{p1}$ (FIG. 9) which flows through thermistor 74, resistive element 12 (i.e., the resistive load), and then thermistor 76. This current flow through thermistors 74 and 76 causes the thermistors to heat rapidly with the result that their resistance increases rapidly. As a consequence of this increase in resistance, the amplitude of the current delivered through thermistors 74 and 76 to the resistive load decreases with time, as illustrated in FIG. 10. This increase in resistance and decrease in current amplitude continues until the resistance of thermistor 74 exceeds that of thermistor 72 and the resistance of thermistor 76 exceeds that of thermistor 78. When this occurs, the current delivered by capacitor 6 will follow path $i_{p2}$ (FIG. 9) which extends through thermistor 72, in the opposite direction through resistive load 12, and through thermistor 78. Thus, at the instant the resistance of the positive temperature coefficient thermistors 74 and 76 exceeds the resistance of the negative temperature coefficient thermistors 72 and 78, the direction of current flow through resistive element 12 changes, i.e., the current flow through the load becomes negative. As the residual portion of the charge on capacitor 6 is discharged, the current amplitude of the waveform increases exponentially approaching the zero amplitude level, i.e., the current amplitude becomes less negative over time.

Thus, by proper selection of the thermal/resistive coefficients of thermistors 72-78 used in circuit 70, the biphasic waveform N illustrated in FIG. 10 may be generated. The specific configuration of waveform N may thus be precisely tailored to the application in which circuit 60 is to be used by appropriate selection of thermistors 72-78.

In one embodiment of circuit 70, capacitor 6 was a 50 microfarad capacitor which was changed to 4,320 volts, the resistive load was 50 ohms, thermistors 74 and 76 had a resistance of 500 ohms at 25° C. and a heat capacity of 0.5 joules/° C., and thermistors 72 and 78 had a resistance of 2 ohms at 25° C., a heat capacity of 0.6 joules/° C. and a transition temperature of 65° C. The load had a resistance of about 50 ohms. The waveform created by this embodiment of circuit 70 is illustrated in FIG. 10, with the current at the beginning of the pulse (i.e., at t=0) being about 78 amps, the polarity of the pulse changing at about 0.75 milliseconds (i.e., time x=0.75 ms), and the maximum amplitude of the negative polarity of the pulse being equal to about −32 amps.

Heat sinks 50, may also be attached to thermistors 72-78 in the manner described above with respect to thermistors 10 and 14. Such use of heat sinks 50 is appropriate when it is desired to increase the rate at which the thermistors 72-78 cool down after heating.

The circuits illustrated in FIGS. 1, 3, 3a, 5, and 9 may be advantageously incorporated in a known manner in a conventional defibrillator 100 of the type disclosed in U.S. Pat. No. 3,814,105 to Howard et al. and illustrated schematically in FIG. 1 1. With defibrillator 100, switches 4 and 8 of the circuits illustrated in FIGS. 1, 3, 3a, 5, and 9 are coupled, respectively, with charge button 102 and discharge button 104. Also, with defibrillator 100, the resistance 12 of the circuits illustrated in FIGS. 1, 3, 3a, 5, and 9 is provided by a patient (not shown) connected to electrodes 106 and 108. It is to be understood that defibrillator 100 includes all the other controls and displays of a modem defibrillator.

Since certain changes may be made in the devices described above without departing from the scope of the invention herein involved, it is intended that all matter contained in the above description or shown in the accompanying drawings shall be interpreted in an illustrative and not in a limiting sense.

The embodiments of the invention in which an exclusive property or privilege is claimed are defined as follows:

1. In a medical instrument for delivering an electrical energy pulse to a patient, wherein the medical instrument includes a source of energy, an energy storage means, a pair of electrodes that are attachable to the patient, and connecting means for connecting energy stored in the storage means to the pair of electrodes, the improvement comprising a current control means connected between the energy storage means and the pair of electrodes for varying over time the current waveform that can flow from the energy storage means to the pair of electrodes to produce a damped sinusoidal current waveform that varies as a function of the temperature of said current control means.

2. A medical instrument according to claim 1, wherein said current control means comprises a self-heating resistive device, the resistance of which decreases in proportion to increases in temperature of the device.

3. A medical instrument according to claim 2, further comprising:
   (a) first switching means, connected between the source of energy and the energy storage means, for selectively coupling the source of energy with, and decoupling the source of energy from, the energy storage means; and
   (b) second switching means, connected between the energy storage mans and the connecting means, for selectively coupling the energy storage means with, and decoupling the energy storage means form, the pair of electrodes.

4. A medical instrument according to claim 2, wherein said current control means further comprises cooling means coupled to said resistive device for dissipating heat from said resistive device.

5. A medical instrument according to claim 4, wherein said cooling means comprises a plurality of fins made from aluminum.

6. A medical instrument according to claim 1, wherein said current control means comprises a thermistor having a negative temperature coefficient.

7. A medical instrument according to claim 1, further comprising shunt means, connected to said connecting means, for shunting a residual portion of the energy delivered from said energy storage means away from the patient when the energy storage means is connected to the pair of electrodes, wherein said residual portion has a magnitude that is a function of a temperature of said shunt means.

8. A medical instrument according to claim 7, wherein said shunt means comprises a resistive device, the resistance of which varies as a function of the temperature of the resistive device.

9. A medical instrument according to claim 7, wherein said shunt means comprises a negative temperature coefficient thermistor.

10. A medical instrument for generating and providing a pulse of electrical energy to a pair of electrodes that are attachable to a patient, the circuit comprising:
    energy storage means, coupleable to an energy source, for storing and discharging a predetermined quantity of energy;
    connecting means, connected to said energy storage means and connectable to the pair of electrodes, such that energy stored in said energy storage means is delivered from said energy storage means to the pair of electrodes; and
    current control means, connected between said energy storage means and said pair of electrodes, for producing over time as a function of the temperature of said current control means a damped sinusoidal current which flows from said energy storage means to the pair of electrodes upon connection of the energy storage means to the pair of electrodes.

11. A medical instrument according to claim 10, further comprising shunt means, connected to said connecting means, for shunting a residual portion of the energy delivered from said energy storage means away form the pair of electrodes when said connecting means is connected to the pair of electrodes, wherein said residual portion has a magnitude that is a function of a temperature of the shunt means.

12. A medical instrument according to claim 10, further comprising inductive means connected between said energy storage means and said pair of electrodes, for storing and releasing a predetermined quantity of energy delivered upon the connection of said energy storage means to the pair of electrodes so as to increase the amount of time required for the energy delivered to the pair of electrodes to reach a peak value.

13. A medical instrument according to claim 10, further comprising cooling means coupled with said current control means for dissipating heat from said current control means.

14. A wave-shaping device for use in a medical instrument that produces an energy pulse and delivers the energy pulse to a patient, the medical instrument including an energy source, energy storage means coupleable to the energy source for storing and discharging a predetermined quantity of energy and a pair of electrodes attachable to the patient, the wave-shaping device comprising:
    self-heating current control means, connectable to the energy storage mans, for producing a damped sinusoidal current waveform delivered from the energy storage means as a function of the temperature of said self-heating current control means; and
    connecting means for connecting said self-heating current control means to the energy storage means and to the pair of electrodes.

15. A defibillator for producing and delivering a damped sinusoidal defibrillation pulse to a patient comprising:
    energy storage means for storing electrical energy;
    electrode means, coupled with said energy storage means, for delivering said defibrillation pulse to the patient; and
    circuit means, coupled with said energy storage means and including a resistive device, for controlling the flow of current delivered from the energy storage means as a function of the temperature of said resistive device so that the flow of current from the energy storage means will vary over time in accordance with a predetermined dampened sinusoidal waveform.

16. A defibrillator according to claim 15, wherein the resistance of said resistive device decreases as the temperature of the resistive device increases.

17. A defibrillator according to claim 15, further comprising shunt means for shunting a residual portion of the current delivered from the energy storage means away from said electrode means wherein said residual portion has a magnitude that is function of a temperature of the shunt means.

18. A medical instrument including a pulse generation circuit for producing and delivering an energy pulse to a patient, comprising:
    energy storage means, coupleable to an energy source, for storing and discharging a predetermined quantity of energy;
    connecting means, coupled to said energy storage means for connecting the energy storage means to a pair of electrodes that are attachable to the patient; and shunt means, connected to said connecting means, for shunting a residual portion of the energy discharged by said energy storage means away from the pair of electrodes when the pair of electrodes is connected to said energy storage means, wherein the residual portion has a magnitude that varies as a function of a temperature of the shunt means.

19. A medical instrument according to claim 18, wherein said shunt means comprises a resistive device, the resistance of which varies as a function of a temperature of the resistive device.

20. A medical instrument for providing a pulse of energy having a dampened sinusoidal, biphasic current waveform to a pair of patient electrodes that are attachable to a patient, the circuit comprising:
   energy storage mans, coupleable to an energy source, for storing and discharging a pulse of energy;
   connecting means, connected to said energy storage means and connectable to the pair of patient electrodes, for carrying a pulse of energy discharged by said energy storage means to the pair of patient electrodes; and
   current control mans, connected between said energy storage means and said pair of patient electrodes, for shaping a pulse of energy discharged by said energy storage means as a function of a temperature of said current control means so that the current delivered by the pulse of energy initially has a damped sinusoidal shape of one polarity and then after a predetermined period of time has a damped sinusoidal shape of an opposite polarity.

21. A medical instrument according to claim 20, wherein said current control means comprises first and second thermistors connectable to the pair of patient electrodes so as to define a first current path, and third and fourth thermistors connectable to the pair of patient electrodes so as to define a second current path, said first and second thermistors having a negative temperature coefficient and said third and fourth thermistors having a positive temperature coefficient.

22. A medical instrument according to claim 20, wherein said current control means comprises a first pair of thermistors having a first set of thermal/resistive characteristics and a second pair of thermistors having a second set of thermal/resistive characteristics.

23. A wave-shaping circuit for use in a medical instrument that produces and delivers an energy pulse to a patient, the medical instrument including energy storage means, couple to an energy source, for storing and discharging a pulse of energy, a pair of electrodes attachable to a patient and means for connecting the energy storage means to the pair of electrodes, the wave-shaping circuit comprising:
   wave-shaping means, coupleable with the energy storage means, for shaping pulses of energy discharged by the energy storage means over time as a function of the temperature of said wave-shaping means so that a current waveform delivered by each pulse varies as a bisphasic damped sinusoid; and
   connecting means coupled with said wave-shaping means for connecting said wave-shaping means to the pair of electrodes.

* * * * *

UNITED STATES PATENT AND TRADEMARK OFFICE
CERTIFICATE OF CORRECTION

PATENT NO. : 5,275,157
DATED : January 4, 1994
INVENTOR(S) : C. B. Morgan et al.

Figure 11:
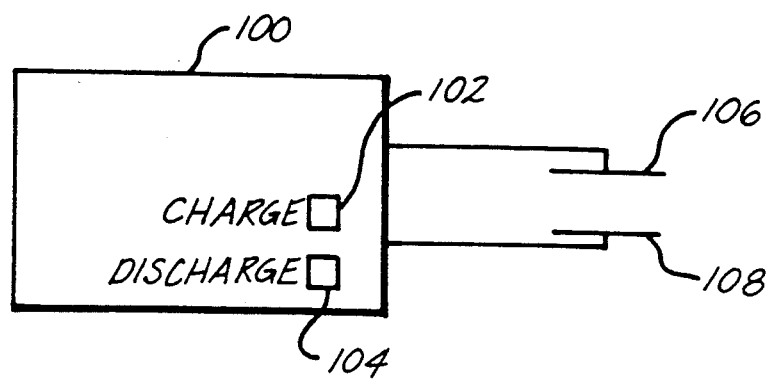
FIG. 11 is a schematic illustration of a defibrillator designed to incorporate a selected one of the various embodiments of the circuit of the present invention.

It is certified that error appears in the above-indentified patent and that said Letters Patent is hereby corrected as shown below:

| COLUMN | LINE | |
|---|---|---|
| 6 | 42 | "FIG. 1 1" should read --FIGURE 11-- |
| 7 (Claim 3 | 21 Line 12) | "form" should read --from-- |
| 8 (Claim 11 | 2 Line 5) | "form" should read --from-- |
| 8 (Claim 14 | 27 Line 10) | "mans" should read --means-- |
| 8 (Claim 17 | 57 Line 5) | after "is" insert --a-- |
| 9 (Claim 20 | 17 Line 5) | "mans" should read --means-- |
| 9 (Claim 20 | 24 Line 12) | "mans" should read --means-- |
| 10 (Claim 23 | 18 Line 4) | "couple" should read --coupleable-- |

Signed and Sealed this

Twenty-fourth Day of May, 1994

Attest:

BRUCE LEHMAN

Attesting Officer

Commissioner of Patents and Trademarks